United States Patent [19]

Remy et al.

[11] 4,231,660
[45] Nov. 4, 1980

[54] MICROSCOPE SLIDE WITH ELECTRODE ARRANGEMENT FOR CELL STUDY, AND METHOD FOR ITS CONSTRUCTION

[76] Inventors: Ernst Remy, Georgenstr. 22, 8000 Munich 40; Andreas Meyer, Herzog-Albrecht-Str. 21, 8011 Zorneding; Ellen Rieske, Thomaweg 12, 8131 Berg II; Günther Gross, Auerbergstr. 9, 8011 Zorneding all of Fed. Rep. of Germany

[21] Appl. No.: 942,305

[22] Filed: Sep. 14, 1978

[30] Foreign Application Priority Data

Sep. 15, 1977 [DE] Fed. Rep. of Germany ....... 2741638

[51] Int. Cl.³ ................. G01N 21/01; G02B 21/34; B32B 3/10; B32B 3/00
[52] U.S. Cl. .................................. 356/244; 350/95; 428/138; 428/195; 428/210; 428/433
[58] Field of Search .................. 350/92, 94, 95; 356/244; 428/137, 138, 457, 433, 209, 210, 195; 156/57

[56] References Cited

U.S. PATENT DOCUMENTS 3,451,880 6/1969 Kay .................................. 428/137 X
3,736,042 5/1973 Markovits et al. .................... 350/95
3,768,914 10/1973 Kinney et al. ..................... 350/95 X
4,139,668 2/1979 Ward .................................. 428/138

*Primary Examiner*—William R. Dixon, Jr.
*Attorney, Agent, or Firm*—Arnold, White & Durkee

[57] ABSTRACT

Disclosed is a slide for supporting matter to be observed under a microscope, including a base, a plurality of electrical conductors disposed on the base, an insulating coating distributed over the base to isolate the matter from the conductor, and a plurality of microscopic perforations through the coating and communicating with the conductors, thereby permitting electrical contact between the conductors and a plurality of precise areas of the matter. The slide further includes a plurality of attraction zones on the surface of the coating adapted to cause matter to accumulate on the slide in a predetermined pattern with respect to the perforations. The slide is manufactured by affixing a plurality of electrical conductors to a base, applying an insulating coating over the base and the conductors, and forming microscopic perforations through the base by focussing a laser beam through the coating and onto a conductor, thereby partially vaporizing the conductor, the resulting vapor pressure causing a microscopic portion of the coating over the conductor to be removed.

16 Claims, 7 Drawing Figures

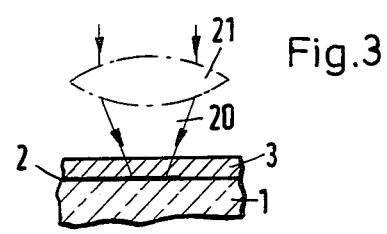
Fig.3
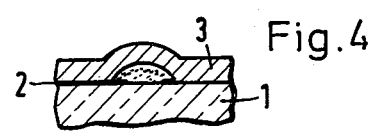
Fig.4
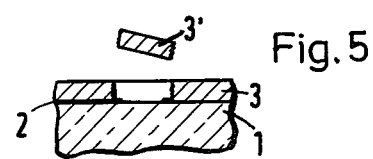
Fig.5
Fig.6
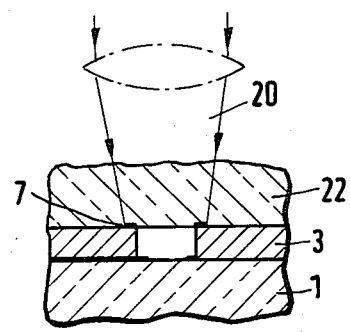
Fig.7
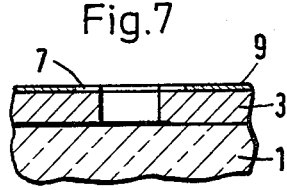

MICROSCOPE SLIDE WITH ELECTRODE ARRANGEMENT FOR CELL STUDY, AND METHOD FOR ITS CONSTRUCTION

BACKGROUND OF THE INVENTION

This invention relates to microscope slides which include electrodes for the examination of organic cells, particularly such slides which are adapted for the study of the electrophysiological behavior of neurons or nerve cells and their processes.

In order to examine the electrophysiological activity of living nerve cells, it is necessary to apply electrical potentials, currents, impulses, etc. to individual cells or to certain parts of a cell, such as the cell processes (neurites), by means of suitable electrodes located in microscopically close proximity to each other. Such electrodes must have contact surfaces of microscopic size, e.g., 1–10 microns, and must present a sufficiently small electrical contact impedance to the cell, as well as exhibiting other characteristics suitable for allowing such electrodes to contact the desired cells or cell areas without harming the cell matter. There have hitherto not been any satisfactory solutions for these requirements, especially where several simultaneous connections on different parts of a small volume of tissue are desired.

It is known, for example, to utilize an electrode consisting of a very thin wire of a hard material, such as tungsten, which is set in a small glass tube. The free end of the wire, which protrudes slightly from the end of the glass tube, is brought into contact with particular areas of the cell by manipulation of the electrode under the microscope. The manufacture of such electrodes, however, is difficult and time consuming. Furthermore, as a rule, the electrodes which are usable must be separated from a large number of defective electrodes produced. Moreover, the three dimensional manipulation of such electrodes under a microscope is very difficult, consequently; the simultaneous manual operation of several electrodes in order to probe various cells or parts of cells at the same time is not practically feasible. Such thin wire electrodes have an additional serious disadvantage in that they vibrate during manipulation, and this motion may cause the death of the cell being studied. Similar objections are applicable to the pipette electrodes, which are filled with an electrolyte, which are known in the art.

SUMMARY OF THE INVENTION

It is a feature of this invention to provide a microscope slide with an arrangement of electrodes, which in a simple manner enables a controlled electrical probe to be made of particular cells or cell areas mounted on the slide and, in particular, enables such electrical contacts to be made simultaneously at a large number of probe locations.

The present invention achieves this purpose by providing a slide with surface areas which form attraction zones having a higher affinity for cells than neighboring areas, and by providing electrical circuitry which connects to these attraction zones.

Preferably the attraction zones are located on the surface of a covering layer or coating, which electrically insulates the circuits and through which are provided microscopically small contact points in the form of perforations which match the pattern of the electrical circuits.

The slide provided by this invention encourages a preferential accumulation of cells at specific points on the slide carrier, which may lead in turn to controlled cell growth which is spatially oriented in accordance with the attraction zones. The invention thus provides a specific spatial correlation between the circuits or their contact points and the cells mounted on the slide. It is thus not necessary to establish electrical contact between an electrode and a cell by manipulation under the microscope; an experimenter may simply observe the cells which have accumulated at an attraction zone under the microscope and then identify the circuit or circuits contacting the cell or parts of the cell which are to be stimulated and use those circuits as electrodes for the desired electrical stimulation. Simultaneous electrical stimulation at several probe points for one or several cells is thereby facilitated.

The advantage gained by the invention goes beyond the provision of such contact points. If the attraction zones are arranged in the form of a netlike pattern or array connecting the electrical contact points, it is possible to encourage an attracted cell, such as a nerve cell, to grow on a slide built in accordance with the invention only in the direction defined by the attraction zones, i.e., the cell will extend its processes (neurites) in directions which can be predetermined by the design of the slide. Thus one may create spatially oriented correlations not only between a cell and multiple contact points, but also between several different cells.

In manufacturing a slide having the electrode arrangement provided by this invention, one may use either a photoengraving process, similar to that commonly used in semiconductor technology, or treatment by lasers in order to produce the perforations in the coating or in the attraction zones to expose the underlying circuits.

The particular and difficult problem of exposing the circuits under each perforation of the coating in a satisfactorily uniform and clean manner, in order to make the transmission impedance sufficiently small between the contact point and a cell, has been solved in this invention by producing the perforations with a laser. The laser is focussed on the electrical conductor under the coating, the beam vaporizes a portion of the material of the conductor, and the resulting vapor pressure blows off the coating just above it. It has been found that this relatively simple process produces uniform perforations of sufficiently small size, i.e., approximately 3 to 10 microns, which completely expose the metallic conductor below them.

The attraction zones can also be produced with a laser. A coating is made of a hydrophobic synthetic resin such as, for example, silicon resin. Free radicals are produced on the surface of the coating by laser irradiation, then polarized or charged molecular groups are deposited in these spots from a solution placed on the coating, so that these areas acquire hydrophilic characteristics and thereby encourage the accumulation of cell matter. Alternatively, the laser can be used to remove a cell-repellent layer from a cell-attracting insulating layer in any desired pattern, and vice versa.

A photoengraving process may also be employed. This process is used to deposit a photolacquer on the coating. This layer is then selectively removed by exposing and developing, thereby creating a screen pattern, which may be used to chemically remove selected areas of the coating below it. In this way, in successive, and to a great extent automated, operations, the conductors, the perforations in the coating above them, and the attraction zones can be constructed by partial removal of a superimposed hydrophilic or hydrophobic layer. Using similar processes one may also manufacture semiconductor circuitry connected with the conductors, particularly with initial stages having field effect transistors (FETs) as impedance modulators, such semiconductors being located on the slide in the same plane as the conductors.

BRIEF DESCRIPTION OF THE DRAWINGS

Additional objects, features, and advantages of the present invention will become apparent by referring to the following detailed description of the preferred embodiments thereof in association with the accompanying drawings, wherein the same reference numerals refer to like elements throughout all the figures.

In the drawings:

FIGS. 3 to 5 show in elevation the steps involved in the preparation of electrical contact points on the slide of FIG. 1 by the method this invention.

FIGS. 6 and 7 illustrate two alternative methods for preparing attraction zones on the slide of FIG. 1.

DESCRIPTION OF THE PREFERRED EMBODIMENTS

Figure 1:
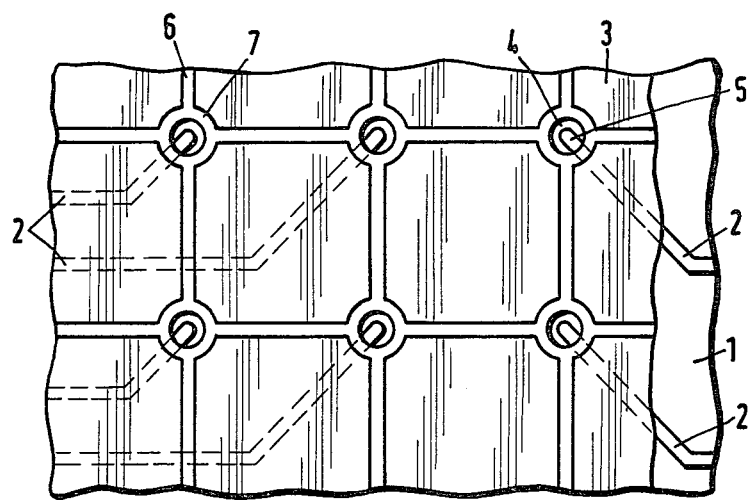
FIG. 1 shows in a partially cross-sectional plan view a high magnified segment of a microscope slide constructed in accordance with the invention.

A microscope slide built in accordance with the present invention, a portion of which is shown highly magnified in FIG. 1, includes a base plate 1, which may be made of glass, quartz, sapphire, silicon or of 3-5 compounds, such as GaP. Distributed over the upper surface of the base plate 1 is a pattern of metallic electrical conductors 2, which are constructed of steam-printed or photoengraved gold strips, preferably about 10 microns wide and 2 microns thick. Between the gold circuit layer 2 and the base plate 1, there may be added an adhesive layer, such as titanium.

Overlaying the conductors 2 is a coating 3, made of a material which will perform adequately as an electrical insulator and which will also exhibit other properties suitable for processing and for cell attraction, as will be discussed further herein. Microscopically small perforations 4 are formed in the coating 3, thereby exposing the ends 5 of the underlying conductors 2 to any matter which may be supported in the upper surface of the coating 3. These ends 5 form a matrix-like pattern or array on the base plate 1, with a spacing between ends which should be in the range of 20 to 200 microns and may amount to 100 microns in any direction.

In the embodiment illustrated in FIG. 1, the perforations 4 are larger in diameter than the width of the circuits 2. The circuits 2, however, may also be made wider than the perforations 4, since it is only necessary to provide an exposed surface on the circuits 2 which is sufficient to establish electrical contact. Nor is it necessary for the perforations 4 to be located at the end points of the circuits 2. The circuits may continue, if desired, beyond a perforation 4. The only design requirement is to provide at least one perforation 4 for each conductor 2.

On the surface of the coating 3 are provided multiple attraction zones 6 and 7. These zones constitute surface areas of the coating which have been treated to exhibit a higher affinity for cells than the untreated areas of the coating 3. The attraction zones 6 and 7 in the preferred embodiment are hydrophilic surface areas, i.e., they are attractive to water, while the remaining surface areas of the coating 3 are hydrophobic, i.e., repellent to water. The attraction zones 7 are arranged to form circular halos around each perforation 4, while the zones 6 are positioned to establish narrow paths, which connect the individual perforations 4 and the halo-shaped zones 7 with each other in a net-like or matrix fashion. In this way a pattern of attraction zones 6 and 7 is created which is spatially correlated to the perforations 4 and to the underlying electrical contact points on the slide.

Other patterns of attraction zones may be envisioned by those skilled in the art. For example, either the paths 6 or the circular halos 7 may be omitted or the paths 6 may be arranged in such a way that the perforations 4 are not situated at the corner points of squares or rectangles as shown, but at the center points of the sides of such designs. Triangular or hexagonal patterns are also possible, depending upon the particular uses contemplated for the slide.

Figure 2:
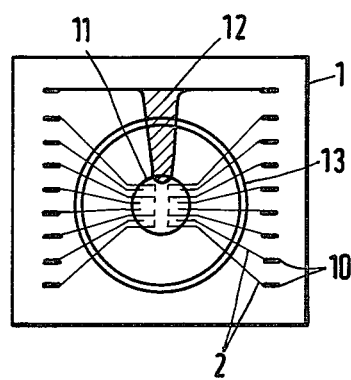
FIG. 2 is a plan view of the slide of FIG. 1, on a reduced scale showing the entire slide.

Now referring to FIG. 2, the complete slide, corresponding to the portion shown in FIG. 1, is illustrated on a reduced scale. The base plate 1 is a square plate and the individual conductors 2 are arranged to travel from the connector contacts 10, located at the outer periphery of the plate 1, to a central area bounded by the circular line 11. Within this central operational area, the conductors 2 form the matrix-like arrangement noted in FIG. 1, and conform to the perforations 4 in the coating 3 and the attraction zones 6 and 7. The thickness of the coating 3 should preferably be as small as possible inside the circle 11 (for example, approximately 2 microns) and should be just thick enough to provide adequate insulation between the circuits 2 and the electrolyte above then (preferably having an impedance of at least 30 megohms, measured at 1 kHz). Outside the circle 11, the coating 3 should have a considerably greater thickness; here there are no perforations or attraction zones. The conductors 2 should be so constructed that they all have approximately the same length from their outer connector contact points 10 to their end or contact points inside the central area 11. They should further be located at approximately equal distances from each other, so that they will not differ in their probe impedance amounts. In addition, the base plate 1 is provided with a large surface reference electrode 12.

At each contact point 10 in the circuits 2, using integrated circuit technology, a preliminary processing stage with impedance modulation, preferably including a field effect transistor, may be installed. A raised ring mounted on the slide defines the area of the slide on which cell cultures, including nutrient liquids, can be placed, and prevents the separation of these materials.

Now referring to FIGS. 3-5, the perforations 4 in the coating 3 are made in the following way. A laser beam 20 is focussed by a microscope objective 21 through the coating 3, which is penetrable by laser rays, and onto the end of a circuit 2. The laser radiation is absorbed by the metal of the circuit 2, the metal thereby becoming sufficiently heated to partially vaporize, as shown in FIG. 4. The energy concentration and exposure time of the laser impulse are so adjusted that the rapidly rising vapor pressure blows out a small piece 3' of the coating 3 located directly above the irradiated point of the circuit 2, before no more than half of the approximately 2 micron thick circuit 2 has been vaporized, as shown in FIG. 5. In this short interval, it has been found that the coating 3 itself will not get hot enough to melt or vaporize. Thus, by means of a purely mechanical blast, a neatly defined perforation 4 is produced, in which the electrically conducting metal of the circuit 2 is completely exposed.

By changing the exposure time or the energy concentration of the laser beam and its focus, the extent to which the metal of the conductor 2 is vaporized and the size of the perforation produced may be adjusted, so that the perforation 4 will have the same or a smaller diameter than the width of the conductor 2, or a larger perforation 4, for example, 20 microns in diameter, can be made with a somewhat stronger laser impulse, which will expose the entire terminal area of circuit 2, as shown in FIG. 1.

To meet the special needs required for use of the slide in cell research, the material of the coating must satisfy the following specific requirements: It must insulate well electrically in a very thin layer and it should have a low dielectric constant in order to maintain the capacitive shunt impedance as high as possible. The material must be chemically neutral and should be sterilizable by ultraviolet radiation or by heating to 200° C. It should adhere well to glass, should have thermal expansion characteristics as much like those of glass as possible, and should be transparent for purposes of microscopic observation.

Furthermore, in order to facilitate the manufacture of the perforations 4, as shown in FIGS. 3 to 5, the material of the coating 3 must necessarily exhibit substantial hardness and brittleness, and low elasticity after hardening, so that the blowouts made by the vapor pressure of the vaporized metal affect a small area of the coating and the coating does not separate elastically from its underlying layer in the form of a large bubble. How small the perforation produced should be depends in each case on the impedance desired.

It has been found that a suitable material for use in forming the coating 7 is a product available under the tradename "Dow Corning 648," which, when used with the adhesive agent Dow Corning 1200, adheres well to glass. Dow Corning 648 is a silicon resin exhibiting the following chemical and physical properties: a viscosity during application of up to 100 Centipoise when properly diluted, a dielectric constant of approximately 3, a disruptive strength of 1800 volts per millimeter, a specific electric resistivity of $10^{15}$ Ohm-centimeters, a colorless appearance, and a fracture expansion of an order of magnitude of about 0.5 to 5%, preferably about 1 to 2%.

In order to prepare a slide according to this invention, a solution of Dow Corning 648 in xylol (6:4) is spread on the base plate 1 by means of a centrifuge at such a thickness that, after drying and hardening at 200° C., it produces a layer 2 to 4 microns thick on top of the conductors. The conductors 2, located between the base plate and the coating, are made of gold in the preferred embodiment, with a thickness of 2 microns. It has been found that the desired perforations may be produced by means of a nitrogen laser having an emission wavelength of 337.1 mm, using single impulses of a 10 nanosecond duration and an intensity per impulse of around $10^{10}$ to $10^{12}$ Watts per square centimeter. For any materials used in the coating 3 it is essential that the fracture expansion be in the neighborhood of a few percent to a few thousandths of a percent. Only fracture expansions in that percentage range will guarantee a neat blastoff of the coating material by the laser, and only above the lower limit can one be sure that the different thermal expansions of the coating material and the carrier will not cause cracks.

The preparation of the attraction zones 6 and 7 can be accomplished, as in FIG. 6, by irradiating the desired areas with a laser beam 20 and thereby chemically activating those areas, so that free radicals are formed on the surface. The irradiation is passed through a solution 22 containing allyl alcohol or an allyl amine, which is applied to cover the coating 3 and from which polarized or charged groups of molecules attach themselves to the free radicals of the irradiated surface areas, thereby forming a hydrophilic surface layer, conforming to attraction zones 6 and 7.

Instead of using a laser, the perforations in the coating and the attraction zones may also be made by means of photoengraving. A particularly suitable material for the coating 3 in this case is silicon oxide. Since this substance exhibits hydrophilic properties, the attraction zones 6 and 7 can be made by covering the coating 3, as in FIG. 7, with a hydrophobic film 9½ microns thick (e.g., a silicon resin) and partially removing this film by the process of photoengraving, so that the pertinent areas of the surface of the coating 3 are uncovered and thus form the attraction zones 6 and 7.

Although typical embodiments of the present invention have been illustrated and discussed herein, further modifications and alternative embodiments of the apparatus and method of this invention will be apparent to those skilled in the art in view of this description. Accordingly, this description is to be construed as illustrative only and is provided for the purpose of teaching those skilled in the art the manner of constructing the apparatus and carrying out the method of the invention. It is to be understood that the forms of the invention shown and described herein are to be considered as the presently preferred embodiments. Various changes may be made in the configurations, sizes, and arrangements of the parts, as will be recognized by those skilled in the art. For example, equivalent elements may be substituted for those illustrated and described herein, parts or connections may be reversed or otherwise interchanged, and certain features of the invention may be utilized independently of the use of other features, all as will be apparent to one skilled in the art after receiving the benefit attained through reading the foregoing description of the invention.

What is claimed is:

1. A slide for supporting an electrically contacting cell matter to be observed under a microscope comprising:

a base;

a plurality of electrical conductors disposed on said base; and an insulating coating applied over said base and said electrical conductors to insulate said cell matter from said electrical conductors; and a plurality of microscopic perforations through said insulating coating, each of said perforations communicating with a respective one of said electrical conductors thereby permitting electrical contact to at least one precise area of said cell matter by stimulation of the respective electrical conductor.

2. The slide of claim 1, wherein said electrical conductors and said perforations are arranged on said slide in a uniform array.

3. The slide of claim 2, wherein each of said electrical conductors extends from an outer electrical contact point near the periphery of said slide, and wherein said perforations and the ends of said electrical conductors remote from said contact points are arranged in a uniform array in a central area of said slide.

4. The slide of claim 3, wherein the thickness of said insulating coating is reduced within said central area of the slide to a thickness presenting a resistance of not less than 30 megohms between said electrical conductors and an aqueous electrolyte containing said cell matter disposed on said insulating coating.

5. The slide of claim 1, wherein said electrical conductors are in the range of 2 and 10 microns in width.

6. The slide of claim 1, wherein said perforations are spaced in the range of 20 and 200 microns apart.

7. The slide of claim 1, wherein said electrical conductors comprise gold foil having a thickness of approximately two microns.

8. The slide of claim 1, wherein said electrical conductors are approximately equal in length and present approximately equal impedances.

9. The slide of claim 1 further comprising a plurality of impedance modulators each formed as an integrated circuit on said slide and connected to a respective one of said electrical conductors.

10. The slide of claim 1, further comprising attraction zones on said insulating coating, said attraction zones having an enhanced affinity for the accumulation of cells thereon.

11. The slide of claim 10, wherein said attraction zones form an array matching with the array of said electrical conductors and perforations.

12. The slide of claim 11, wherein each said perforation is surrounded by a respective attraction zone.

13. The slide of claim 11, wherein said attraction zones are formed as paths interconnecting said perforations.

14. The slide of claim 10, wherein said insulating coating is hydrophobic and said attraction zones are formed by a hydrophilic layer formed on part of the surface of said insulating coating.

15. The slide of claim 10, wherein said insulating coating is hydrophilic and the surface thereof is covered by a hydrophobic layer in those areas not forming the attraction zones.

16. A slide for supporting cell matter to be observed under a microscope, comprising:
a base; and
attraction zones on said base, said attraction zones having an enhanced affinity for the accumulation of said cell matter thereon.

* * * * *